(12) United States Patent
Hoffman

(10) Patent No.: US 6,516,804 B1
(45) Date of Patent: Feb. 11, 2003

(54) CARDIO-THORACIC COMPRESSION HARNESS

(75) Inventor: Jon F. Hoffman, Oroville, CA (US)

(73) Assignee: Aztec-Life, Inc., Oroville, CA (US)

( * ) Notice: Subject to any disclaimer, the term of this patent is extended or adjusted under 35 U.S.C. 154(b) by 0 days.

(21) Appl. No.: 09/916,846

(22) Filed: Jul. 27, 2001

Related U.S. Application Data

(63) Continuation-in-part of application No. 09/563,371, filed on May 3, 2000, now abandoned.

(51) Int. Cl.[7] .................................................. A61F 5/37
(52) U.S. Cl. .......................... 128/846; 128/875; 602/19
(58) Field of Search ................................. 128/846, 869, 128/874, 875, 876; 602/13, 19

(56) References Cited

U.S. PATENT DOCUMENTS

| | | | | |
|---|---|---|---|---|
| 1,650,650 A | * | 11/1927 | Pieper | 128/78 |
| 4,633,876 A | * | 1/1987 | Scullin | 128/460 |
| 4,715,362 A | * | 12/1987 | Scott | 128/878 |
| 5,111,806 A | * | 5/1992 | Travis | 602/19 |
| 5,724,993 A | * | 3/1998 | Dunfee | 128/874 |

* cited by examiner

Primary Examiner—Michael A. Brown
(74) Attorney, Agent, or Firm—The Kline Law Firm

(57) ABSTRACT

A cardio-thoracic compression harness that includes a pair of bands are placed around the body of the user so as to compress and hold in place the thorax, sternum, and ribs. The device is positioned so that the bands contact the user's body above and below the breasts. This allows a female user to wear the device while wearing a bra. The device can also be constructed as a device integral to an undergarment such as a bra. The device includes a plurality of closures so that it can conform easily to the shape of the user's body. The device may also include shoulder straps for more secure positioning. The harness can be worn under or over the user's clothing.

8 Claims, 6 Drawing Sheets

CARDIO-THORACIC COMPRESSION HARNESS

This application is a continuation-in-part of co-pending U.S. application Ser. No. 09/563,374, filed May 3, 2000 now abandoned.

FIELD OF THE INVENTION

This invention relates generally to medical support devices, and more particularly is a post-operative open heart and thoracic surgery elastic assisting device to reduce pain while allowing increased upper torso movement, particular that of the arms and shoulders, that reduces the transfer of energy and usage of chest wall musculature when performing upper arm and body tasks.

BACKGROUND OF THE INVENTION

In 1996, according to the American Heart Association, there were 753,345 open heart procedures performed in the United States alone. That number does not include other sternotomy procedures. The essential access to the heart in performance of a cardiac procedure is obtained by cutting the patient at mid-chest from the collar bone to the solar plexus, (approximately 12 inches), and then opening the chest cage at that mid-point. The chest cage is opened by spreading the rib cage so that access to the heart and lungs is obtained. Closure of the chest cage is accomplished by placing the sternum in its original position and binding it with surgical wire, then suturing the approximately 12 inch skin opening. There is no casting of the area and the only means of ensuring closure of the sternum break to allow healing/regeneration is the surgical wire. Upper arm and torso movement, such as that required when opening doors, gripping rails on treadmills, tieing shoes, rolling during sleep, etc., causes substantial discomfort for which pain reducing drugs are prescribed.

The known prior art is relegated to the protection of the wearer from outside forces to the body such as described in "Shock Absorbing Athletic Equipment", by Donzis, U.S. Pat. No. 4,513,449, issued Apr. 30, 1985. This device essentially contains padded air pockets to absorb the impact. Further known prior art is a "Rib Protector", by Whiteside et al., U.S. Pat. No. 5,337,417, issued Aug. 16,1994. The device disclosed in this reference is also is an impact absorption device consisting of movable, substantially rigid plates in pockets which distribute the impact load. One additional prior art device that is somewhat related to the field of the present invention is the "Protector and Article of Sportswear Using the Same", by Kato, et al., U.S. Pat. No. 5,337,418, issued Aug. 16, 1994. This device also is an impact device containing air cushions and rigid ribs.

A medical device used on the upper body of the patient is the "Ambulatory Lumbo-Sacral Traction Systems and Methods", by Scott, U.S. Pat. No. 4,715,362, issued Dec. 29, 1987. This device encircles a user under the arms and adjacent the pelvis. The device is used to apply traction and as a shock absorber, but discloses no means to provide a compression force on the user's chest region. A medical device that does provide a means of compression is the "Patient-Activated Body Immobilizer and Method of Use", by Williams, Jr., U.S. Pat. No. 4,641,642, issued Feb. 10, 1987. This device hangs loosely about the patient's upper body, and is activated by the user applying pressure.

There are no prior art devices adapted to laterally and continually compress the chest wall in any manner, which isolates the pectoral muscles from pulling on the severed sections, thereby allow the post-operative or post-trauma patient to move more comfortably while healing. The current medical practice is to issue the patient a pillow to hold across his chest when trauma to the chest is imminent. Using this method, the patient loses the ability to use his arms. Further, this method cannot be used while the patient is sleeping (when coughing or sneezing can still occur). Medical journals have recognized the shortcomings of the "pillow-to-the-chest" method, and have explored methods to provide post-operative thoracic support, including internal fixation.

Accordingly, it is an object of the present invention to provide a device that continually compresses and holds in place the thorax and sternum post-surgery.

It is a further object of the present invention to provide a device that is adjustable by the user.

It is a further object of the present invention to provide a device that maintains pressure even when the patient is sleeping.

It is a still further object of the present invention to provide a device that is simple and inexpensive to manufacture.

SUMMARY OF THE INVENTION

The present invention is a cardio-thoracic compression harness that comprises at least one horizontal stretchable band applied to the thorax of the user. Preferably, a pair of bands are placed around the body of the user so as to compress and hold in place the sternum and thorax. The device is positioned so that the bands contact the user's body above and below the breasts. This allows a female user to wear the device while wearing a bra. The device can also be constructed as a device integral to an undergarment such as a bra. The device includes a plurality of closures so that the device can conform easily to the shape of the user's body without compressing breast tissue. Each band of the harness has an independent closure which permits adjustments, medical examination, and use of monitoring devices without releasing all the support of the harness. The harness may also include shoulder straps for more secure positioning. The device can be worn under or over the user's clothing.

An advantage of the present invention is that it provides a means of adjustable compression, applicable by either the health-care provider or the patient, to the cardio-thoracic region of a post-trauma patient.

Another advantage of the present invention is that it can be worn either over or under the user's clothing.

A still further advantage of the present invention is that it can be used in conjunction with a shoulder harness to hold the device more securely in place.

A further advantage of the present invention is that it provides a device that maintains pressure even when the patient is sleeping.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

Figure 1:
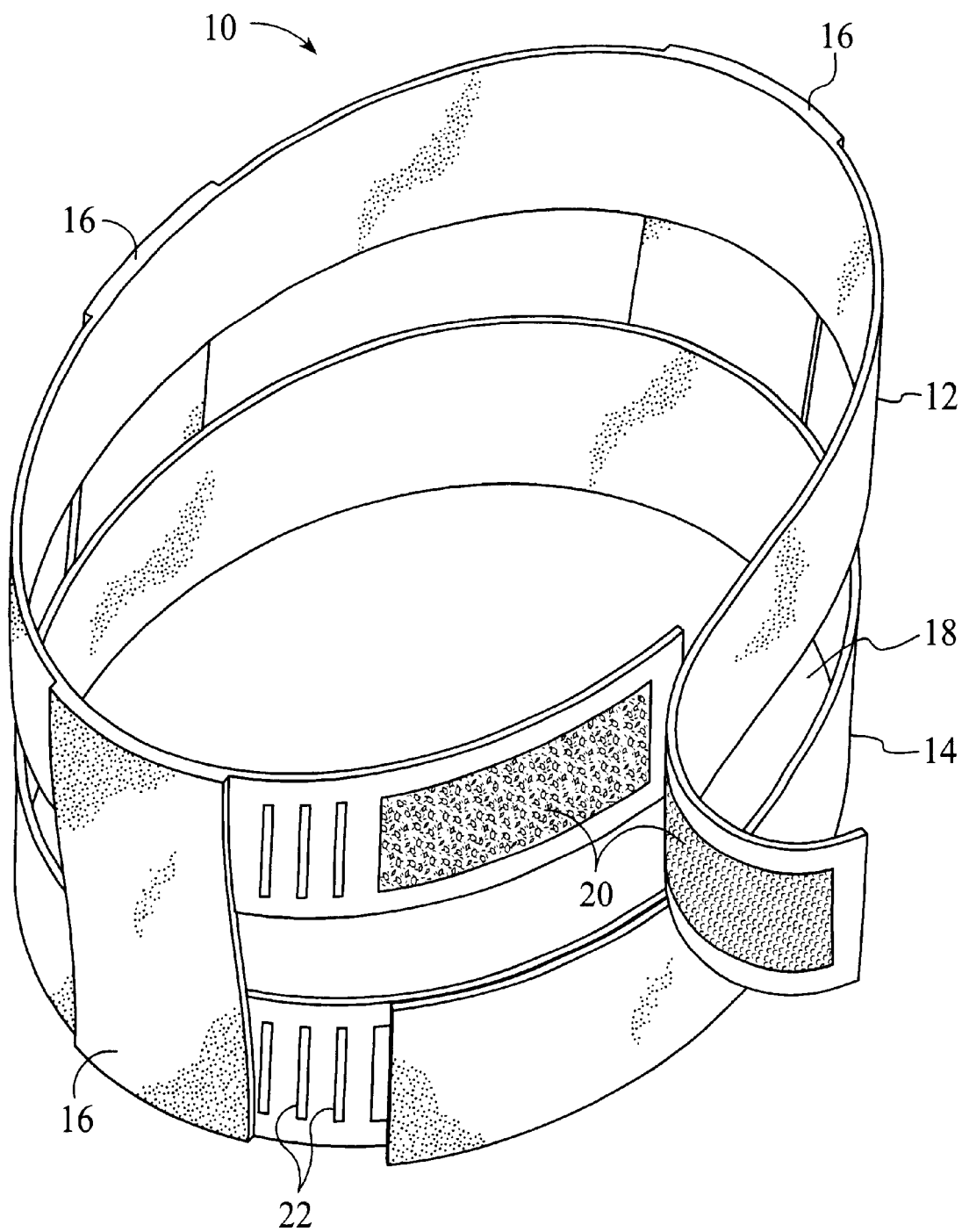
FIG. 1 is a perspective view of the cardio-thoracic compression harness of the present invention.
Figure 2:
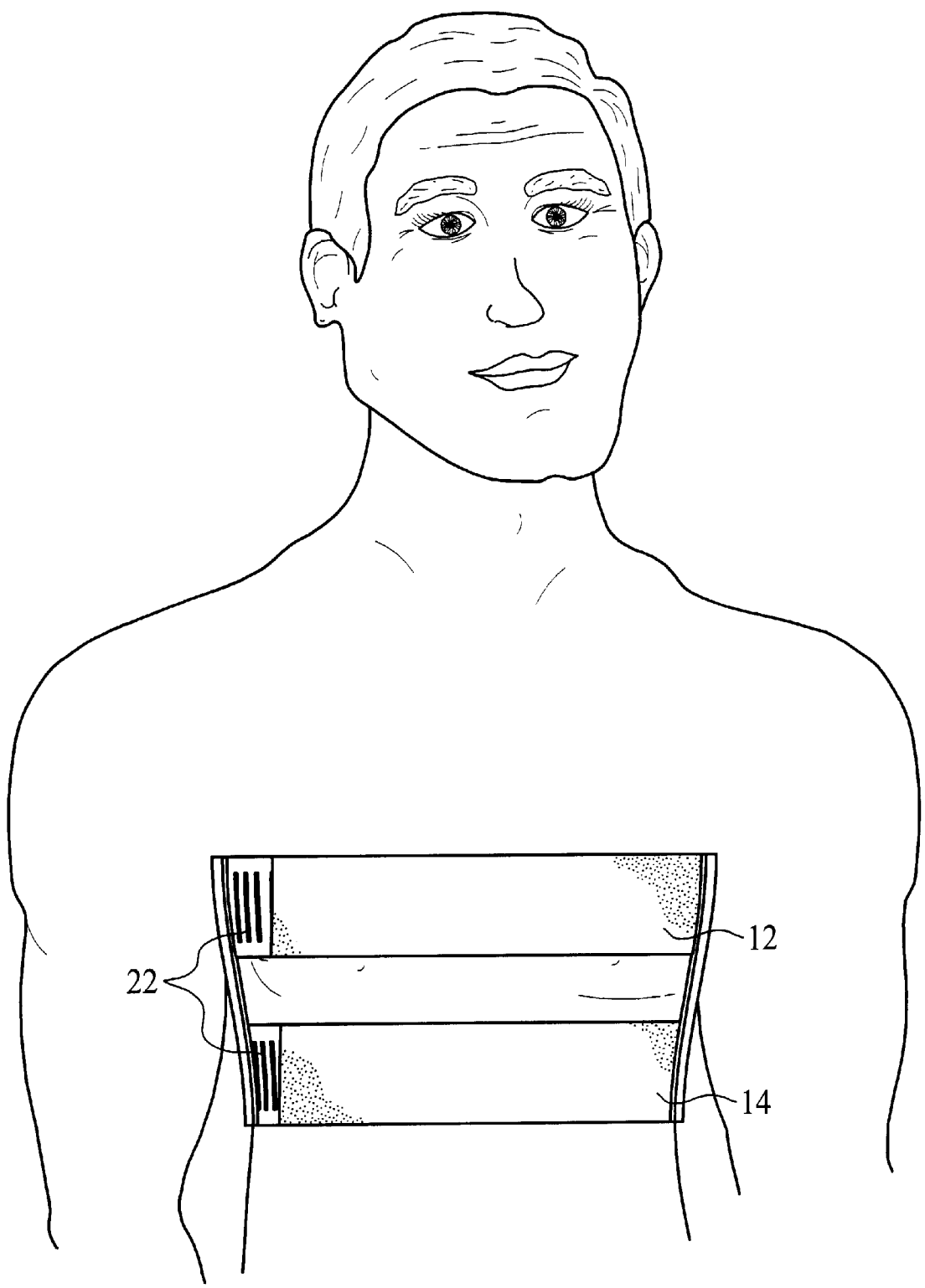
FIG. 2 is a front view of a user wearing the cardio-thoracic compression harness.
Figure 3:
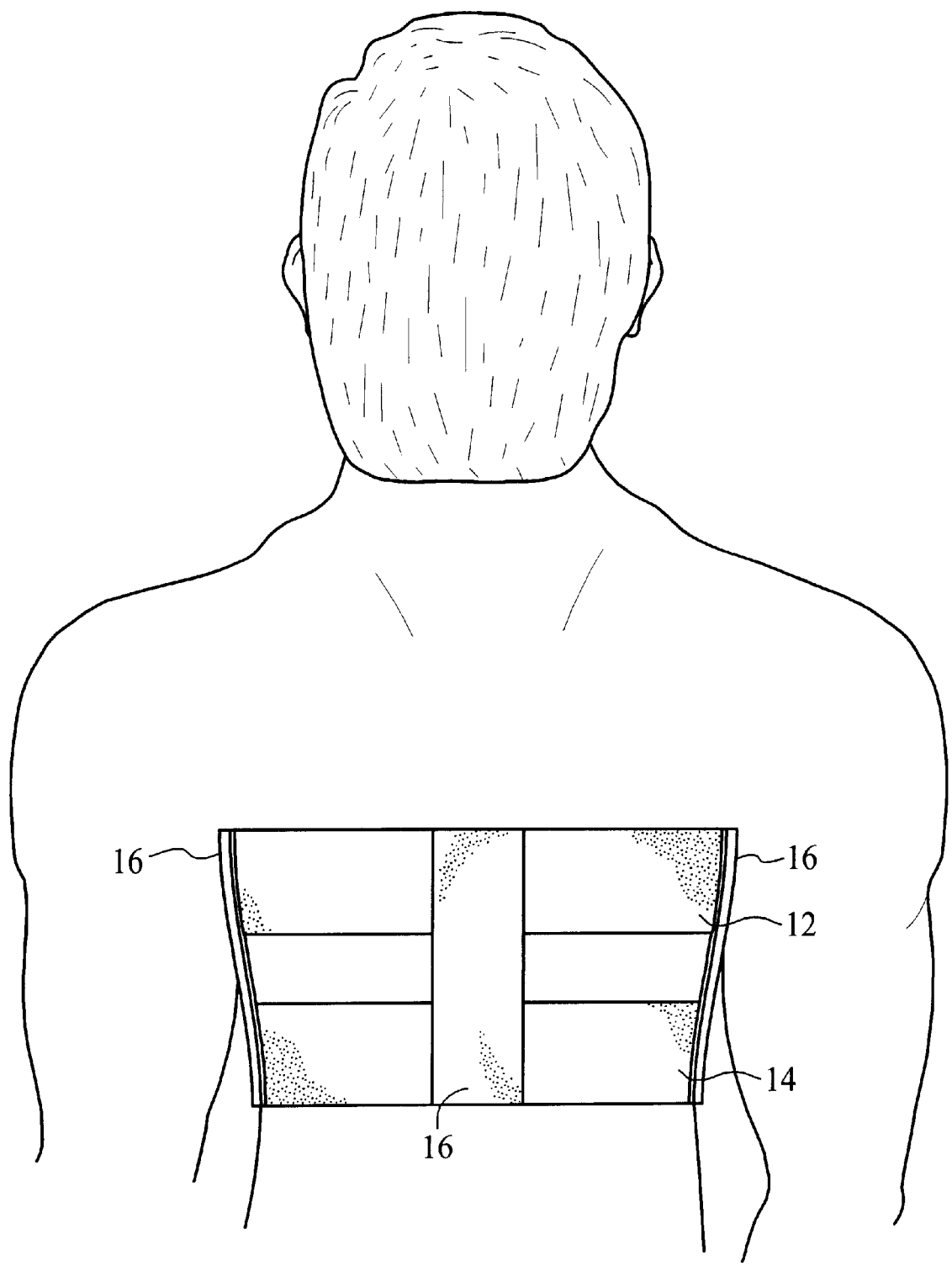
FIG. 3 is a rear view of a user wearing the cardio-thoracic compression harness.

Referring first to FIGS. 1–3, the present invention is a cardio-thoracic compression harness 10. The compression harness 10 comprises an upper encircling band 12 and a lower encircling band 14. The upper and lower encircling bands 12, 14 are joined by flexible, non-weightbearing vertically oriented connecting elements 16. The bands 12, 14 can be formed from nearly any material, but function best if they are made from stretchable fabric. This allows the bands 12, 14 to apply constant pressure to the thorax region. In the preferred embodiment, the bands 12, 14 are approximately 3 inches wide. This thickness provides the wearer comfort and prevents the bands from rolling. The thickness of the bands 12, 14 further provides for more skeletal contact through the skin and musculature than wider bands which are essentially flesh compressors with minimal thoracic impact. The bands 12, 14 are sufficiently wide to accommodate monitors, bandages, dressings, and/or pad inserts as deemed appropriate by the treating physician. The bands 12, 14 may be of various thicknesses, or they may be folded as a laminate to provide additional pressure, comfort, and/or control.

The compression harness 10 is constructed with an open mid-region 18 formed between the upper and lower bands 12, 14. The open mid-region 18 provides ventilation to the area of the wound, and also provides an accommodation for female users of the An device. The open mid-region 18 accommodates a female user's breasts so that the compression harness 10 can be worn comfortably by women. If desired, the harness 10 can be manufactured as an integral component of a bra.

The connecting elements 16 can also be formed from nearly any material, but it has been determined in development efforts that the connecting elements 16 function best if formed from a stretchable, non-rigid material. Any number of connecting elements 16 can be utilized. In the preferred embodiment, connecting elements 16 are provided at a central rear position and at two equally spaced positions on two sides to correspond to the locations of the user's arms. Moreover, in the preferred embodiment, a specific provision is that no connecting elements 16 are provided on a front side of the compression harness 10 in order to minimize contact with the users incision area.

The encircling bands 12, 14 are constructed with free ends joined by fastening means 20 so that the user can easily put on the device. The free ends of the bands 12, 14 and the fastening means 20 are offset from center to minimize the contact with the incision area of the user which enhances both comfort and medical care. While it is easily recognized that many types of fastening elements can be used with the compression harness 10, the simplest and most efficient fastening means 20 is VELCRO.

Using VELCRO allow the user to quickly and easily secure the device when the user is putting on the compression harness 10. The VELCRO fasteners also allow the user to adjust the pressure applied by the compression harness 10 at a moment's notice. This is a feature that is particularly useful when the user becomes aware of impending shock to his thorax, such as an approaching bump in the road while driving, or a sneeze or cough. The user simply grasps the free ends of the bands 12, 14, and pulls them to the desired tension.

To facilitate compression adjustment of the compression harness 10, a plurality of incremental markings 22 is provided at the connecting region of the bands 12, 14, that is, the region where the top free ends overlap the lower free ends of the bands 12, 14.

The incremental markings 22 allow the user to consistently reproduce a compression level that is comfortable, and to determine how much extra compression to apply in the event of impending shock to the thoracic region. The user simply notes which of the markings 22 are covered by the free ends of the bands 12, 14 for a given compression level, and he is then able to easily reproduce that compression level when desired.

Figure 4:
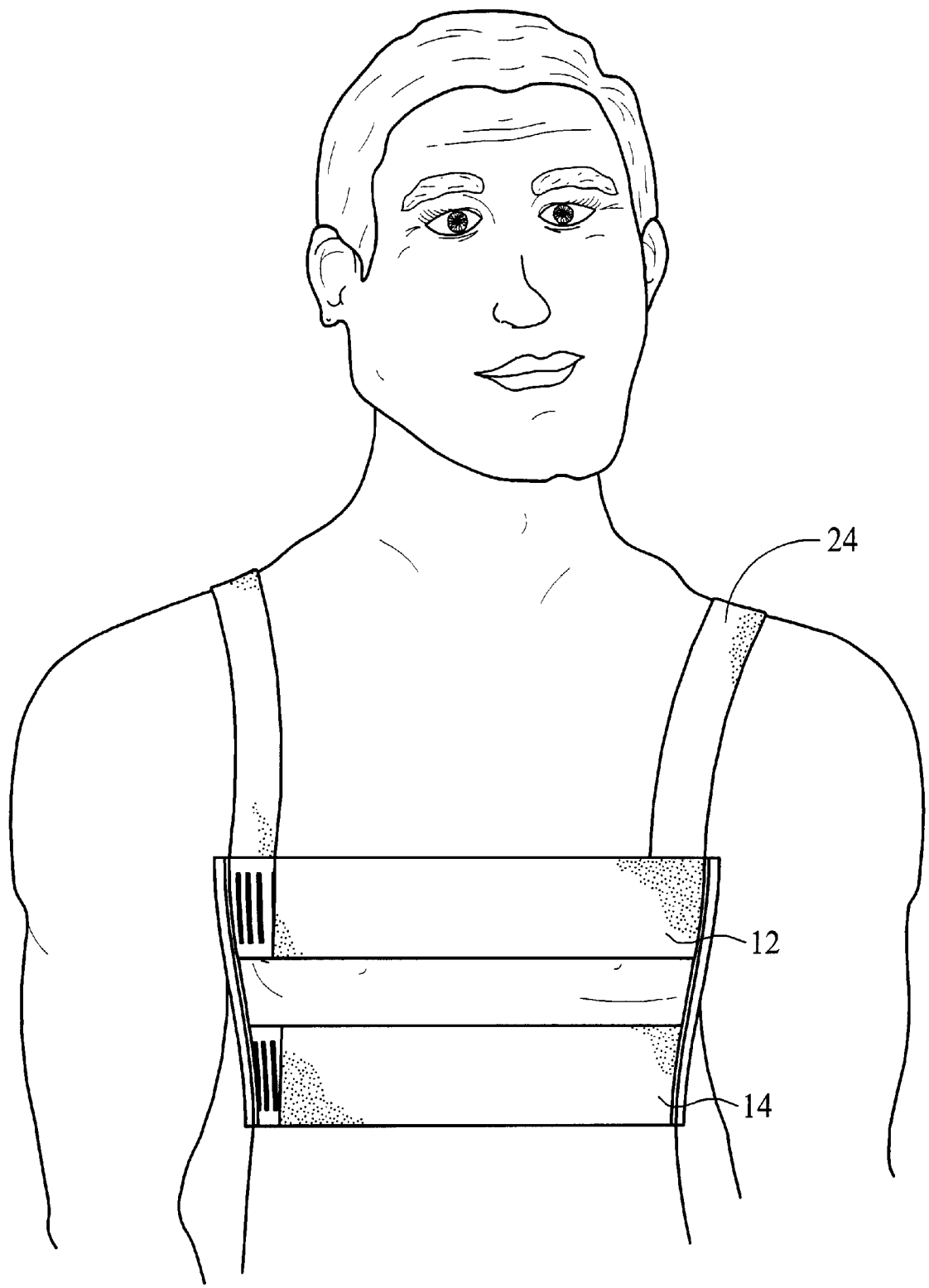
FIG. 4 is a front view of a user wearing the cardio-thoracic compression harness with shoulder straps included.
Figure 5:
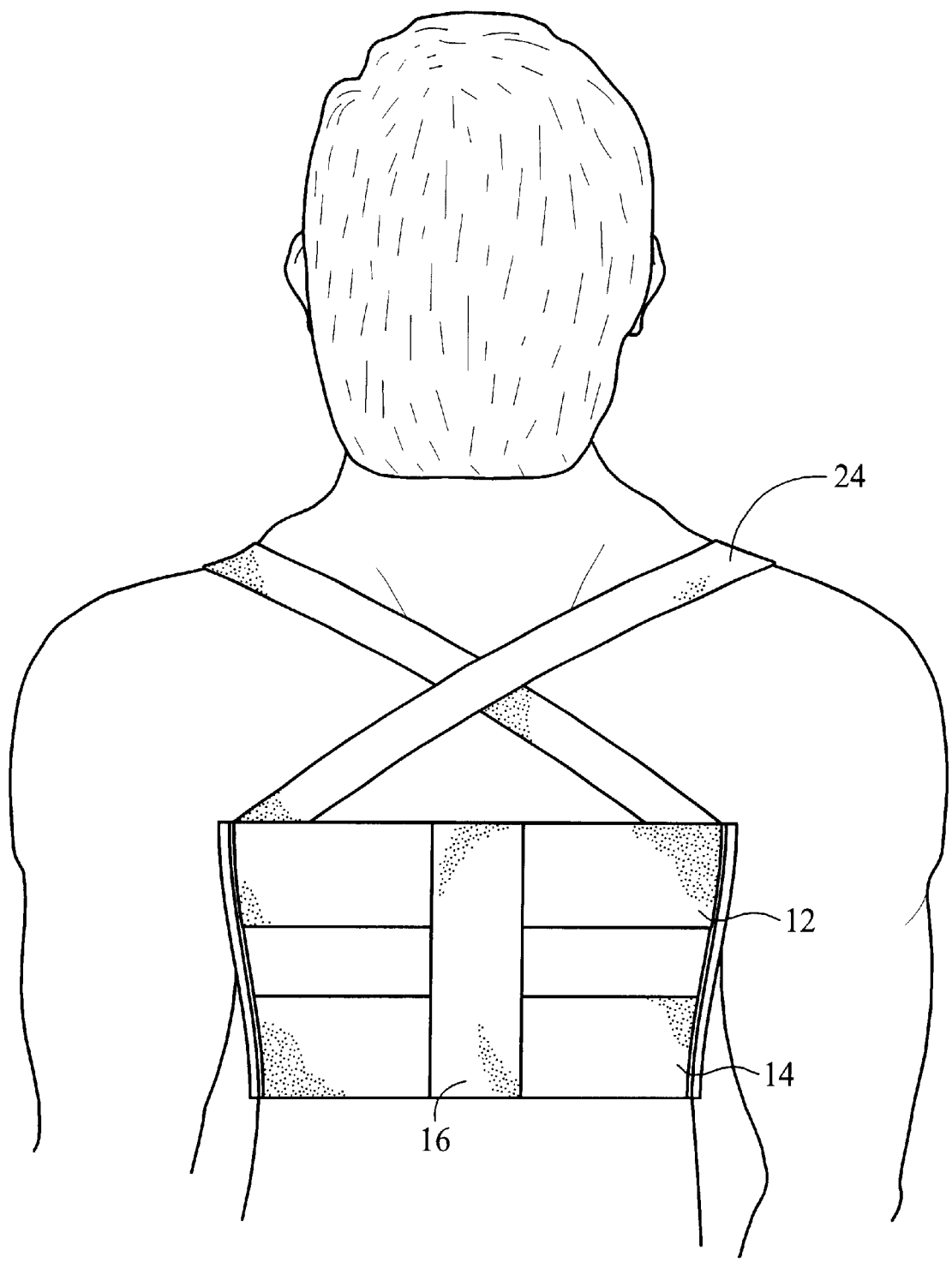
FIG. 5 is a rear view of a user wearing the cardio-thoracic compression harness with shoulder straps included.

The compression harness 10 of the present invention may also be further secured by the use of one or more shoulder straps 24 as illustrated in FIGS. 4–5. The shoulder straps 24 may be crossed in the rear as shown in FIG. 5, or they may simply pass straight over the user's shoulders. The shoulder straps 24 may be either permanently attached to the compression harness 10, or they may be removably attached for optional use. The shoulder straps 24 also include length adjustment means.

If additional local support is desired for a specific application of the device, such as for the protection of injured ribs, additional connecting elements 16 can be applied as desired. For this type of application where additional localized support is needed, it is envisioned that the connecting elements 16 would be removably attached to the encircling bands 12, 14.

Figure 6:
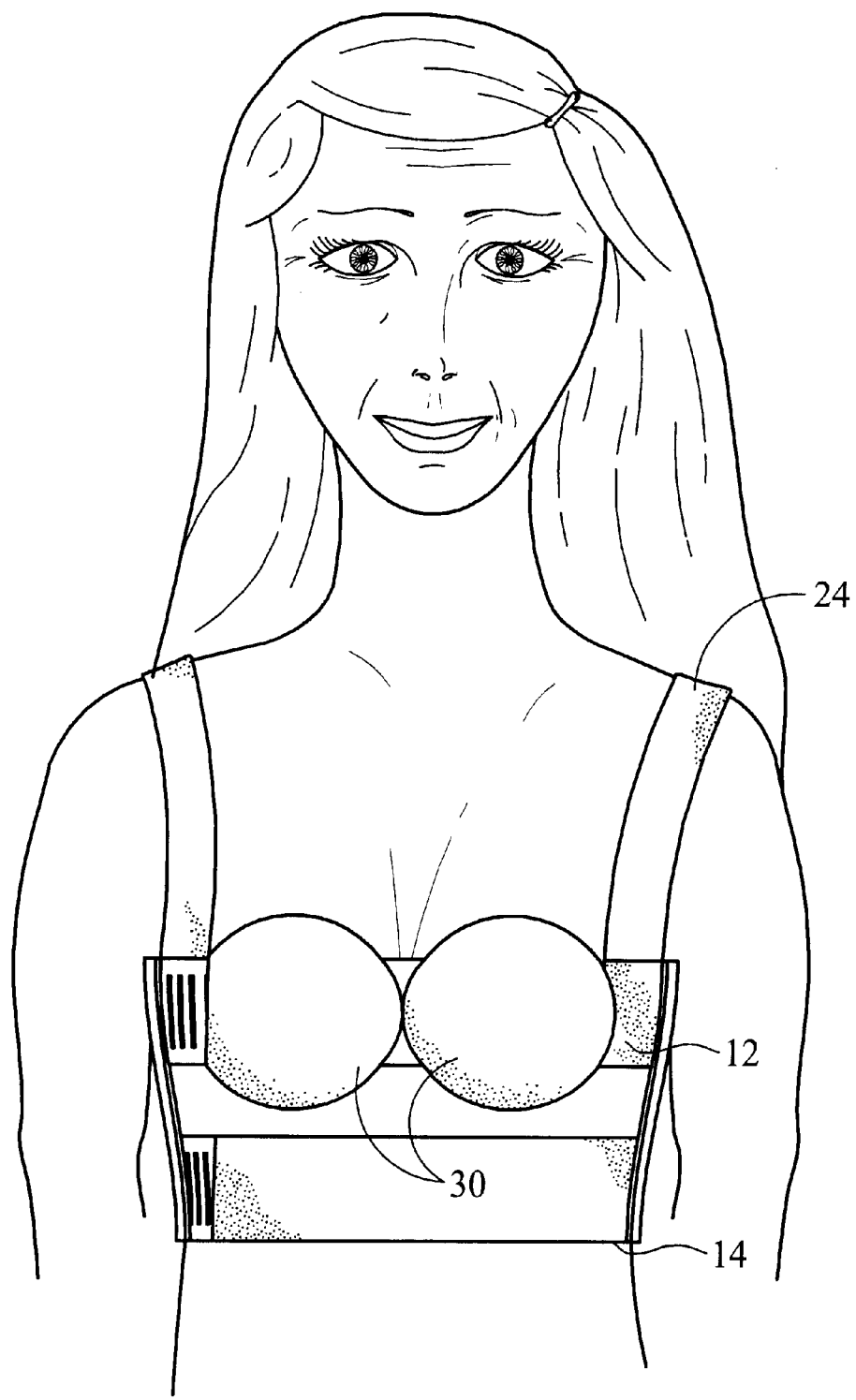
FIG. 6 is a perspective view of the device including bra cups.

As illustrated in FIG. 6, the compression harness can be designed to include bra cups 30. This enables a female user of the device to benefit from the compression characteristic of the device, but to increase considerably her comfort while wearing the harness.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A cardio-thoracic compression harness comprising:
    an upper encircling band and a lower encircling band, both said upper encircling band and said lower encircling band being positioned around a chest region of a user, said upper and said lower bands are joined by flexible connecting elements, said upper and said lower bands are separated by an open mid-region crossed by said connecting elements, with no connecting elements being positioned in a front section of said mid-region so as to avoid contact with an incision area of a user, and
    free ends of said upper and said lower bands are adjustably joined by fastening means so that constant and variable pressure is applied to the thoracic region of the user, said fastening means being located at a side of said harness to avoid contact with the incision area of the user.

2. The compression harness of claim 1 wherein:
    said upper and said lower bands are made from stretchable fabric.

3. The compression harness of claim 1 wherein:

said harness further comprises a means to adjust a compression level of said harness.

4. The compression harness of claim 3 wherein:

said means to adjust said compression level of said harness comprises a plurality of incremental compression adjustment markings, so that the user is able to accurately reproduce a desired compression level.

5. The compression harness of claim 1 wherein:

said harness further comprises at least one shoulder strap.

6. The compression harness of claim 5 wherein:

said at least one shoulder strap is removably attached to said harness.

7. The compression harness of claim 5 wherein:

said harness further comprises bra cups so that said harness is worn as a bra.

8. A cardio-thoracic compression harness comprising:

an upper encircling band and a lower encircling band, both said upper encircling band and said lower encircling band being positioned around a chest region of a user, said upper and said lower bands are joined by flexible connecting elements, said upper and said lower bands are separated by an open mid-region crossed-by said connecting elements, with no connecting elements being positioned in a front section of said mid-region so as to avoid contact with an incision area of a user, and bra cups so that said harness is worn comfortably by a female user; wherein free ends of said upper and said lower bands are adjustably joined by fastening means so that constant and variable pressure is applied to the thoracic region of the user, said fastening means being located at a side of said harness to avoid contact with the incision area of the user.

\* \* \* \* \*